(12) United States Patent
Lee et al.

(10) Patent No.: US 8,372,353 B2
(45) Date of Patent: Feb. 12, 2013

(54) SAMPLE PROCESSOR

(75) Inventors: Martin Alan Lee, Wiltshire (GB); David James Squirrell, Wiltshire (GB); Michael John Withers, Cambridge (GB); Trevor John Beckett, Cambridge (GB); Christopher John Silk, Cambridge (GB)

(73) Assignee: Enigma Diagnostics Limited, Wiltshire (GB)

( * ) Notice: Subject to any disclaimer, the term of this patent is extended or adjusted under 35 U.S.C. 154(b) by 173 days.

(21) Appl. No.: 12/671,839

(22) PCT Filed: Aug. 1, 2008

(86) PCT No.: PCT/GB2008/002625
§ 371 (c)(1),
(2), (4) Date: Mar. 11, 2010

(87) PCT Pub. No.: WO2009/019448
PCT Pub. Date: Feb. 12, 2009

(65) Prior Publication Data
US 2010/0180980 A1    Jul. 22, 2010

(30) Foreign Application Priority Data

Aug. 3, 2007  (GB) .................................. 0715171.5

(51) Int. Cl.
*B01L 3/00*     (2006.01)
(52) U.S. Cl. ....................................................... 422/500
(58) Field of Classification Search .................... 422/500
See application file for complete search history.

(56) References Cited

U.S. PATENT DOCUMENTS

| | | | |
|---|---|---|---|
| 3,614,434 A * | 10/1971 | Horwitz et al. | 250/364 |
| 4,475,411 A * | 10/1984 | Wellerfors | 73/864.24 |
| 4,928,539 A * | 5/1990 | Champseix et al. | 73/864.24 |
| 5,219,526 A | 6/1993 | Long | |
| 5,279,796 A * | 1/1994 | Parker et al. | 422/510 |
| 5,364,790 A | 11/1994 | Atwood et al. | |
| 5,669,524 A * | 9/1997 | Loedel | 220/9.1 |
| 5,720,923 A | 2/1998 | Haff et al. | |
| 6,016,712 A * | 1/2000 | Warden et al. | 73/864.21 |
| 6,190,617 B1 * | 2/2001 | Clark et al. | 422/562 |
| 6,228,657 B1 * | 5/2001 | Genovese et al. | 436/167 |
| 6,255,478 B1 | 7/2001 | Komai et al. | |
| 6,274,087 B1 | 8/2001 | Preston et al. | |
| 6,281,008 B1 * | 8/2001 | Komai et al. | 435/306.1 |

(Continued)

FOREIGN PATENT DOCUMENTS

| | | |
|---|---|---|
| CA | 20927442 C | 8/2001 |
| DE | 203 00 998 U1 | 3/2003 |

(Continued)

OTHER PUBLICATIONS

English machine translation of EP0263753A1. 3 pages. Jun. 7, 2012.*

(Continued)

*Primary Examiner* — Bobby Ramdhanie

(57) ABSTRACT

A sample delivery system comprising (i) a cartridge comprising a body section adapted to hold a sealed sample vessel so as to fix the position of a seal of the sample vessel in relation to the cartridge; and (ii) apparatus adapted to receive said cartridge, said apparatus being provided with an opening system for opening said sealed sample vessel contained within the cartridge.

18 Claims, 7 Drawing Sheets

U.S. PATENT DOCUMENTS

| | | | |
|---|---|---|---|
| 6,391,541 B1* | 5/2002 | Petersen et al. | 435/5 |
| 6,403,038 B1 | 6/2002 | Heermann | |
| 6,706,519 B1 | 3/2004 | Kellogg et al. | |
| 6,973,718 B2 | 12/2005 | Sheppard, Jr. et al. | |
| 2002/0050456 A1 | 5/2002 | Sheppard et al. | |
| 2003/0059823 A1 | 3/2003 | Matsunaga et al. | |
| 2004/0020310 A1 | 2/2004 | Escal | |
| 2004/0166502 A1 | 8/2004 | Lai et al. | |
| 2005/0042142 A1 | 2/2005 | Sentoh | |
| 2005/0059161 A1* | 3/2005 | Anderson et al. | 436/174 |
| 2005/0150314 A1 | 7/2005 | Staples et al. | |
| 2006/0024211 A1* | 2/2006 | Giter et al. | 422/104 |
| 2007/0149863 A1 | 6/2007 | Padmanabhan et al. | |
| 2007/0292941 A1* | 12/2007 | Handique et al. | 435/288.7 |

FOREIGN PATENT DOCUMENTS

| | | | |
|---|---|---|---|
| DE | 10 2004 050575 B3 | | 1/2006 |
| EP | 0263753 A1 | | 4/1988 |
| EP | 0564970 A | | 10/1993 |
| FR | EP0263753 A1 | * | 4/1988 |
| GB | 2333250 A | | 7/1999 |
| JP | 2003-164279 A | | 6/2003 |
| WO | WO98/24548 A1 | | 6/1998 |
| WO | WO 98 57180 A | | 12/1998 |
| WO | WO9857180 A1 | | 12/1998 |
| WO | WO9904239 A2 | | 1/1999 |
| WO | WO99/33559 A1 | | 7/1999 |
| WO | WO01/41931 A2 | | 6/2001 |
| WO | WO01/87768 A2 | | 11/2001 |
| WO | WO2004/045772 A2 | | 6/2004 |
| WO | WO2004/055522 A1 | | 7/2004 |
| WO | WO2005019836 A2 | | 3/2005 |
| WO | WO 2005 059929 A | | 6/2005 |
| WO | WO2005059929 A2 | | 6/2005 |
| WO | WO 2006101833 A2 | | 3/2006 |
| WO | WO2006042826 A1 | | 4/2006 |
| WO | WO2006/130408 A2 | | 12/2006 |
| WO | WO2007/082466 A1 | | 7/2007 |
| WO | WO2009019453 A2 | | 2/2009 |

OTHER PUBLICATIONS

Office Action for U.S. Appl. No. 12/671,257. Date Mar. 28, 2012. 13 pages.*

International Search Report for PCT/GB2008/002630 (International Publication No. WO2009/019453 A2) dated Jun. 4, 2009 (8 pages).

International Search Report for PCT/GB2008/002625 (International Publication No. WO2009/019448A8) dated Jul. 7, 2009 (7 pages).

Search Report dated Nov. 28, 2007 for Application No. GB0715171.5 (4 pages).

Young et al, "PDMS-based micro PCR chip with Parylene coating", J. Micromech. Microeng.13 (2003) 768-774 (8 pages).

C.A. Harper, ed., Handbook of Plastics and Elastomers, p. 1-82ff, McGraw-Hill, NY, 1975 (3 pages).

Parylene and NOVA TRAN® World-Class Parylene Coating Services', product brochure, Specialty Coating Systems/Alpha Metals, Inc., 1995 (6 pages).

Parylene Conformal Coatings Specifications and Properties', product brochure, Specialty Coating Systems/Alpha Metals, Inc., 1997 (12 pages).

* cited by examiner

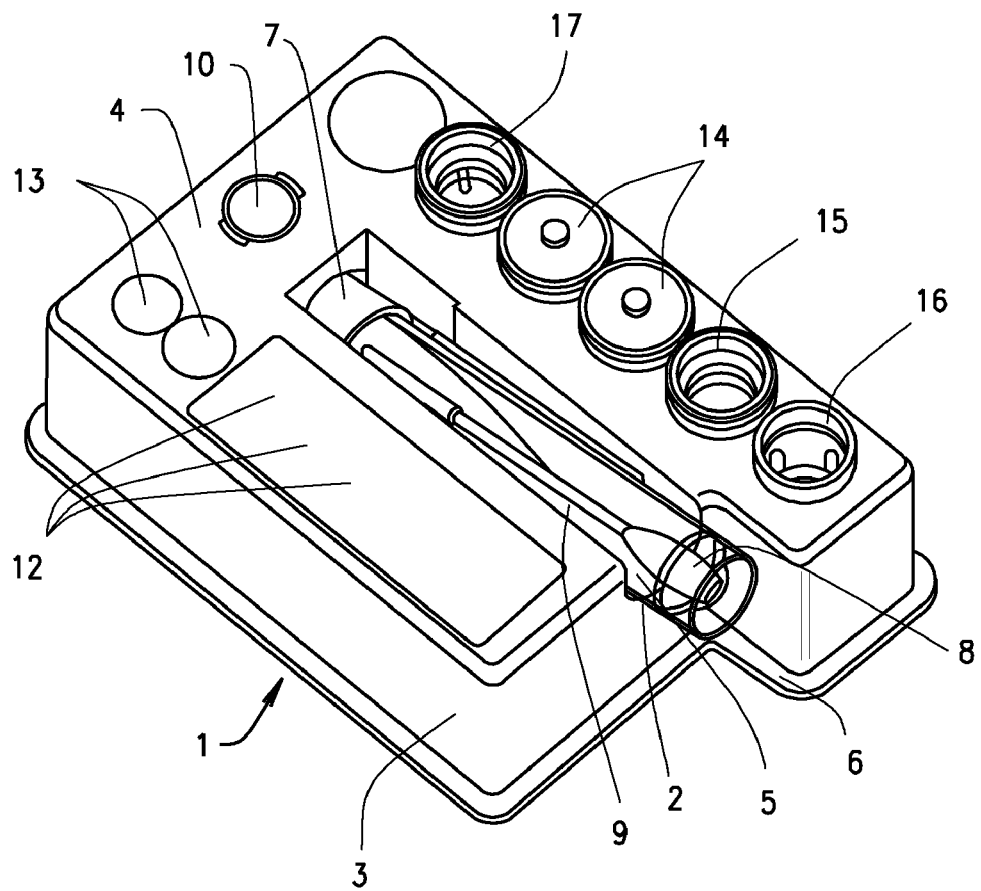
F I G . 1 1

SAMPLE PROCESSOR

This application is a U.S. national stage application of PCT international application PCT/GB08/02625, filed on Aug. 1, 2008, which claims priority to United Kingdom Patent Application No. 0715171.5, filed on Aug. 3, 2007.

FIELD OF INVENTION

The present invention relates to a device for handling samples, in particular clinical samples in preparation for analysis, for instance by means of a nucleic acid amplification method, in particular the polymerase chain reaction (PCR), as well as novel elements and procedures which may be utilised in such devices.

BACKGROUND OF INVENTION

The analysis of fluid samples, for example clinical or environmental samples, may be conducted for several reasons. One current area of interest is the development of a method for positively identifying biological material in a fluid sample, for example a clinical or environmental sample. Such a method would allow for early diagnosis of disease states, which in turn would enable rapid treatment and infection control, or the identification of environmental contaminants and the like. There are many techniques by which very sensitive analysis of samples can be carried out including for example nucleic acid amplification techniques such as the polymerase chain reaction (PCR).

However, the very sensitivity of these techniques mean that they are subject to problems with contamination, as even small amounts of contaminants can mask or give false positive results.

In general, the analysis of clinical or environmental samples is carried out in laboratories or in mobile equipment or analytical devices which may be some distance from the site of collection of the sample. This means that samples need to be collected for example by an operative, and placed in a sealed sample vessel for transport to the analytical device. Once delivered to the analytical device, for example, in a laboratory, the sample vessel is usually opened by a further operator, and the contents removed, for example using a pipette which may be carried out manually or by machine, and placed in a reaction chamber to allow analysis to occur. There is a greater risk that contamination may occur at this stage, in particular since a laboratory or analytical environment is most likely to be contaminated by the target analyte, for example the target nucleic acid.

SUMMARY OF THE INVENTION

According to the present invention there is provided a system for delivering a sample, said system comprising
(i) a cartridge comprising a body section adapted to hold a sealed sample vessel so as to fix the position of a seal of the sample vessel in relation to the cartridge; and
(ii) apparatus adapted to receive said cartridge, said apparatus being provided with an opening system for opening a sealed sample vessel contained within the cartridge.

By ensuring that the seal of a sample vessel is only broken once the sample vessel is contained within the apparatus, the risk of contamination from an operator or from the surroundings in the laboratory or in the area of the analytical device is reduced. The breaking of the seal can be accomplished automatically by the operation of the apparatus. The use of a cartridge to precisely position the seal of the sample vessel means that the opening system of the apparatus is able to accurately and effectively interact with it.

The sealed sample vessel may be supported in the body section of the cartridge directly, but in a preferred embodiment, a holder is provided, which can accommodate the sample vessel, and it is then the holder which is insertable into the body section.

The holder is suitably specifically shaped to accommodate the sample vessel. In particular, it may be shaped so that the sample vessel itself is substantially enclosed within the holder. The holder, and preferably the entire cartridge is suitably made from a rigid and durable material such as rigid polymer. When such a material is used to substantially enclose a sample vessel, it provides a further degree protection against accidental breach of the sample vessel, which may be important where this is of a relatively fragile or brittle material such as glass.

Suitably the seal of the sample vessel comprises a plastics or rubber cap, which is preferably held in position by a locking action or screw thread so that it is not easily dislodged. In a particular embodiment, the cap has a piercable membrane such as a rubber membrane or a laminated metal foil in an upper surface of the cap, to facilitate opening once inside the apparatus.

In a particular embodiment, the sample vessel comprises a sealable tube. The dimensions of the tube are suitably such that it may accommodate not only liquid samples of the desired volume, but also if required, swabs.

In this case, the holder is also generally tubular in shape, but with a slightly larger diameter than that of the tube and so that it may fit snugly within the holder. In a particular embodiment, when the tube is sealed with a cap, the diameter of the cap is greater than that of the tube, and also of the internal diameter of the holder, so that, when in position in the holder, the cap rests on the top of the holder. This allows for accurate positioning of the tube within the holder and thus within the cartridge.

A swab support with a swab attached may be integral with the cap of a tube of this type. In this embodiment, in use the cap may be removed for a swab sample to be taken. The swab is then returned to the tube together with sufficient transport medium, or diluent such as sterile water or elution buffer to immerse the swab sample in the tube. The cap is then secured. The swab will generally remain immersed in liquid at this time. Simple shaking of the sealed tube will ensure that at least some sample material is transferred from the swab into the liquid.

Alternatively the swab may be provided as a separate component as part of a sampling kit. These are available with a plastics snap-off feature enabling the swab section to be conveniently separated from the handle section. The shorter, snapped off swab section may then be transferred into the foiled tube containing the transport medium, diluent or elution buffer and treated as above.

Suitably, the holder is integral with or may otherwise be retained within suitable retaining elements on the body of the cartridge in a sample vessel receiving position, in which a sealed sample vessel can be readily inserted into it. However, it should be moveable with respect to the body from a sample vessel receiving position to a closed position in which the desired position of the seal of the sample vessel in relation to the cartridge is achieved. For example, the holder may be pivotal between a sample vessel receiving position and a closed position, or it may be simply lifted manually from the retaining elements on the body and inserted into, for example a suitable recess such as an aperture or channel within the body section of the cartridge, which forms the closed position.

In a particular embodiment, the sample vessel is fixable in the closed position by means of a locking mechanism, such as a snap fit tongue or flange, fitted onto a holder where present, and arranged to engage in a slot provided in the body section of the cartridge.

Suitably, once in the closed position, the seal of the sample vessel is covered and is suitably substantially completely enclosed by the cartridge, holder and/or locking mechanism and so is no longer accessible for removal or breach by an operator. Thus in a particularly preferred embodiment, the locking mechanism, such as the snap fit tongue or flange effectively covers the seal of the reaction vessel once in the closed position, so that it is effectively substantially enclosed by the body section and the tongue or flange.

The locking mechanism is suitably arranged so that it will not operate until the sample vessel is correctly inserted into the holder, where present. This ensures that the seal of the sample vessel is accurately and reliably positioned within the cartridge.

The opening system may take various forms depending upon the nature for example of the sealed sample vessel and the configuration of the apparatus for example. In particular, the opening system provides a means for breaching the seal of the sealed sample vessel, for example by removal or breach of a cap of the sealed sample vessel. In a particular embodiment, the opener comprises an actuator for moving the sample vessel, for example within the holder so as to force the seal of the sealed reaction vessel into piercing contact with a piercing element.

For example, the piercing element may be a needle and piercing of the seal by the needle is facilitated in this case if the seal comprises a piercable membrane as discussed above. In a preferred embodiment, the piercing element comprises a plastics hypodermic needle-shaped tube formed in a recess with an annular seal that interfaces with the face or outside of the sample tube so as to prevent unwanted leakage of the sample material.

Once opened within the apparatus, the sample may be subject to chemical, physical, biochemical, analytical or assay procedures as required. At least some of these may be carried out in the sample vessel itself, but more usually, the sample will be transferred to one or more reaction chambers for further processing. In this case, a delivery device for delivering a liquid sample contained within the sample vessel to a reaction chamber is suitably provided.

The reaction chamber may be provided in the apparatus or it may be contained on the cartridge, depending upon the configuration of the apparatus and the cartridge.

Similarly, the delivery device may be integral with the apparatus or the cartridge, depending upon the nature of the opening system.

In a particular embodiment, both the reaction chamber and the delivery device are contained on the cartridge, so that at least the first subsequent processing steps are conducted on the cartridge.

In a particular embodiment, a piercing needle or piercing element which either forms part of the opening system of the apparatus or, where provided in the cartridge, acts in conjunction with the opening system of the apparatus to breach the seal, forms the delivery device. The piercing needle or piercing element used comprises an internal channel and the end of the needle or piercing element remote from the piercing end is positioned in the reaction chamber. In this way, when the piercing needle or piercing element enters the sample vessel, liquid sample may flow directly out through the same needle or piercing element into the reaction chamber, so ensuring that the sample is enclosed and protected from contamination from the surroundings for as long as possible. A second needle or piercing element, situated above the first, may be employed in parallel where the second needle or piercing element allows the passage of air to displace the liquid drained from the sample tube.

The liquid sample may be drawn along the delivery device such as the piercing needle or piercing element for instance using a reduced pressure or vacuum. However, preferably the cartridge and the apparatus are configured so that when a sample vessel is in position within the cartridge and the cartridge is in position within the apparatus, the sample vessel is inclined with the piercable end lower than the base of the tube so that the liquid flows under the action of gravity out through the delivery device.

Suitably, the delivery device is arranged to ensure that a predetermined volume of sample is delivered to the reaction chamber. This may be achieved by the incorporation of liquid measurement devices within or associated with the delivery device. However, when the delivery device comprises a gravity fed piercing needle or piercing element as described above, a predetermined sample volume can be delivered by ensuring that the volume of liquid placed in the sample vessel during the collection stage is constant (within a set range), and then ensuring that the needle or piercing element enters the sample vessel such that an open end is in a predetermined and appropriate relationship to the meniscus of the liquid within the sample vessel.

In a particular embodiment, both the delivery device, such as the piercing needle or piercing element, and the reaction chamber are contained within the cartridge. In this arrangement, care needs to be taken to ensure that a sealed sample vessel may not inadvertently come into seal-breaching contact with an element of the opening system such as the piercing needle or piercing element prior to the initiation of the opening system within the apparatus. This may be done by using a holder for the sealed sample vessel and ensuring that the actuator is of a relatively small cross sectional area, and the holder is provided with an opening of a size which is sufficient to allow access to the actuator only. In this way, an operator's fingers for example, may be excluded from the inside of the holder so that inadvertent movement of the sample vessel within the holder may be avoided. Suitably also the sample vessel fits into the holder in a snug manner, so that movement with respect to the holder and towards any piercing needle or piercing element can only take place under the action of direct pressure from the actuator. Furthermore, the nature of the seal, for example the thickness of the rubber membrane is selected so that it is only piercable by the needle or piercing element when a significant amount of direct pressure, such as that supplied by the actuator of the apparatus, is applied.

The apparatus suitably contains further elements which allow the analysis or further investigation of the sample to be continued. Thus it may for example include elements suitable for carrying out a variety of chemical or biochemical reactions, analysis or assays on the sample. For instance, the apparatus may comprise a device which carries out sample preparation procedures to make samples such as clinical or environmental samples suitable for procedures such as immunoassays or nucleic acid amplification reactions. In particular the apparatus may contain all the elements required both to prepare the sample and to carry out the subsequent analysis.

An example of apparatus of this type is contained for example in WO2005/019836 the content of which is incorporated herein by reference.

The cartridge also suitably contains further elements which are useful in the subsequent procedures to which the sample are required to be subjected.

Such further elements may include one or more reagent chambers for holding reagents or materials required to continue the analysis of the sample. These reagents or materials, which include wash solutions, diluents or buffers as well as reagents used in the subsequent procedure, are suitably predispensed into the reagent chambers.

Where this involves sample preparation, for example to extract nucleic acid from samples suspected of containing cells, such reagents may include lysis reagents for example chaotrophic salts, bacteriophage, enzymes which may lyophilised, detergents, antibiotics the like. Where the subsequent procedure involves sample analysis, other reagents such as dyes, antibodies, enzymes (including for example polymerase enzymes for PCR), buffers, salts such as magnesium salts, may be included in further reaction chambers on the cartridge. However, the range of possible reagents is very large and they will be selected on a "case-by-case" basis, depending on the nature of the chemical or biochemical reaction or analysis or assay to which the sample is subjected.

The reagents may be present in solid or liquid form. When they are predispensed in solid form, these may be as a solid powder, bead, capsule or pressed tablet form, or they may be adhered to magnetic particles or beads, such as silica beads as is well known in the art.

Reagent chambers containing predispensed reagents are suitably sealed for example using foil seals which may be piercable within the apparatus using cutters. These may be integral with the apparatus, but in a particularly preferred embodiment, a cutter is removeably housed in the cartridge, for example within an appropriately shaped recess or aperture in the body section, so that it is available for use in relation to the particular chemical or biochemical reaction, analysis or assay being carried out.

Other mechanical elements in addition to the cutter, in particular those which may be of a disposable nature, which are useful in or otherwise facilitate further chemical or biochemical reaction, physical processing, analysis or assay of the sample, may also be removeably housed on the cartridge. Such elements may include devices required to move samples, reagents or materials from one chamber to another, such as pipettors, magnets or sheaths therefore, as well as small devices such as filters, stoppers, mixers, caps etc. which may require to be introduced into chambers in the course of the chemical, biochemical or analytical procedures or assays.

Particular examples of suitable pipettors are described in WO 2007/028966 the contents of which are incorporated therein by reference, whereas examples of sheaths for magnets useful in transferring magnetic beads or particles and thus any reagents attached thereto are described for example in WO2005/019836.

If desired also, processing components such as heaters, sonicators etc. which may be required to treat reagents or reagent mixtures to ensure that they are in a desired physical state and any time during the procedure, may also be removeably housed on the cartridge.

Mechanical elements such as cutters, pipettors, magnets or sheaths therefore, as well as other sheaths as detailed more fully below, and processing components as described above, will collectively be referred to hereinafter as "moveable components".

In such cases, the apparatus is provided with means for accessing these moveable components and for moving them as necessary so that they can fulfil the required function in the chemical, biochemical, analytical or assay procedure. In particular, the apparatus may comprise a moveable arm which is able to interact with any moveable component on the cartridge.

The moveable arm, which is for example, a robotic arm, is suitably provided with a grab device, so that it can pick up any moveable components housed on the cartridge and lift it up out of its associate recess or aperture. Suitable grab devices are known in the art. The may include forked elements which are arranged to removeably interact with appropriately positioned flanges on the moveable components, but may also comprise controllable grabbing arms, able to close around an exposed upper portion of one of the moveable components. Again, the moveable components may include particular adaptations such as flanges or recesses which are arranged to interact with grabbing arms to facilitate movement.

The apparatus is designed such that a moveable component held on the arm may be positioned above an appropriate reaction or reagent chamber within the cartridge. The arm may be moveable laterally as well as vertically in order to achieve this. However, in a particular embodiment, the arm itself is moveable only in a single dimension which is vertically, and a transport means for the cartridge is provided, suitably as part of the apparatus, so as to allow it to be moved in a lateral direction that the arm may be positioned directly above each element on the cartridge including reaction chambers, reagent chambers as well as moveable components, so as to allow the desired sequence of events to occur.

When electrically operated processing components such as a heater or sonicators are supplied in this way, it may be useful if the connection between the processing component and the arm of the apparatus were also to provide an electrical connection sufficient to provide power to the processing component during use. However, such elements may be more conveniently housed within the apparatus itself, and arranged to be delivered for example to the appropriate chamber on the cartridge at the required time. The arm itself or an adjunct to the arm on which the processing component such as the heater or sonicator is fitted, may be used in order to ensure that the component can be positioned as necessary in relation to a chamber on the cartridge.

Where components such as sonicators or heaters are fitted to the apparatus in this way, they are generally intended for repeated use and for immersion in a sample, in particular a liquid sample within a chamber.

This in itself, may cause some problems as the use of a non-disposable device in such a way that it comes into direct contact with a sample liquid brings the risk of contamination. Over time, these components may become soiled or tarnished, thus increasing the risk of such contamination.

The applicants have found that this risk can be minimized by placing a sheath, which is disposable, over the processing component before use. In particular, where a processing component such as a heater is used repeatedly during a particular chemical, biochemical procedure or assay, a new disposable sheath is suitably applied on each occasion.

Sheaths of this type are suitably removeably housed on the cartridge in a similar manner to the mechanical elements described above, so that they are readily available and can be accessed and positioned using the arm in a similar fashion. Thus, for example, the sheath may be provided with a lip or flange, able to interact with a fork on the moveable arm of the apparatus and lifted into position around the processing component as necessary.

After use, they may be returned to the cartridge for disposal or disposed of directly.

The sheath is suitably made of a plastics or elastomeric material, and where they are intended for use in conjunction with reusable heaters, they are preferably made of a thermally conducting plastic, for example plastic filled with boron nitride or a commercially available "cool polymer" material, so as to minimize any loses in heater efficiency.

Such sheaths form a further aspect of the invention.

Where heaters are provided in the apparatus, they suitably incorporate temperature sensors, so that the temperature of a reagent or sample in which they are immersed can be determined. When a sheath as described above is used, some calibration of the apparatus will be necessary to ensure that these readings are accurate.

In a particular embodiment, where the apparatus includes both a magnet to facilitate removal of beads or particles from one chamber to another, a heater may be incorporated into the magnet so that the same element may fulfil both functions. For example, heating elements may be incorporated into a core of a bar magnet and this may be used both for the transport of beads or particles, or the heating of vessel or chamber contents.

In that instance, any disposable sheath utilised to cover the magnet when it is deployed in the apparatus is suitably of a heat conducting polymer as described above. Such combined magnet/heaters form a further aspect of the invention.

The apparatus may also comprise devices such as thermal cyclers, optical readers such as fluorimeters, as well as data processing devices arranged to collect, analyse and/or record signals from any chamber within the cartridge or apparatus. The selection and arrangement of suitable devices within the apparatus will depend upon the nature of the chemical and biochemical reaction or assay being conducted, and will be within the ambit of the skilled person.

The inclusion of multiple moveable components and chambers on a cartridge opens up the possibility that the sample preparation and/or analysis may be carried out in a largely self-contained unit comprising the cartridge. Such units, including where all chambers are moveable components, may be readily disposable after use to avoid further contamination risks. Furthermore, by conducting an assay in a single cartridge, it is possible to reduce the risk of errors in sample labelling since the cartridge itself may be labelled at the time of introduction of the sample, for example using a standard bar code labelling system, and the label will remain with the sample throughout the analytical procedure.

All processes are suitably carried out automatically by programming the apparatus to move the relevant components, reagents etc. into contact with each other in an appropriate sequence. For example, as described in WO2005/019836 the sample can be subject to a nucleic acid extraction procedure, followed by a PCR reaction. However, many other procedures in which safe sample delivery is required may be undertaken using the invention by appropriately designing the apparatus and programming it accordingly. The application of such robotic techniques is well known in the art.

When the process includes a thermal cycling step such as a PCR, the apparatus will suitably include a thermal cycling device. The vessel in which the thermal cycling is carried out may be positioned on the cartridge if required. However, alternatively, where the arrangement of the cartridge and the apparatus is such that the preparation of the sample only is carried out on the cartridge, a particularly suitable arrangement is that the prepared sample ends up in a removeable reaction chamber, which is transferred to a specific thermal cycling area (as illustrated for example in WO2005/019836). However, this may not always be necessary and the incorporation of a chamber which may be thermally cycled on the cartridge would be advantageous in that it would allow further simplification of the apparatus.

Use of electrically conducting polymer as a heater for thermal cycling in particular in PCR reactions, as described and claimed in WO 9824548 (the content of which is incorporated herein by reference), provides a particularly compact and versatile system for use in conjunction with the system of the present application, since the ECP may be readily incorporated into a reaction chamber which is housed, if necessary removeably housed) on the cartridge.

Generally, the ECP is used to coat a reaction vessel which comprises essentially two parts, a relatively wide-mouth upper section for receiving the sample, and a lower sealed capillary tube which then acts as the reaction vessel. At least the lower sealed capillary tube comprises ECP which effectively acts as a highly controllable resistance heater, when electrical contacts are placed across it.

In particular, the reaction vessels used to carry out PCR reactions in particular rapid PCR reactions comprise a capillary tube. Capillary tubes, open at both ends, are used routinely to acquire defined volumes of (eg blood) samples for analysis. They are self-filling by capillary attraction and are generally used as a transfer means.

Capillary tubes are used for rapid PCR applications to provide the optimum profile for heat transfer by providing a minimised distance from the sample to the source of heating or cooling. (Flattened tube formats may also be used for the same reason). Because they need to contain and prevent evaporation from aqueous samples that are being heated, these capillary tubes are sealed at one end, filled and then stoppered.

Filling such capillaries with one end closed presents a problem: surface tension holds the sample to the walls of the tube making a seal that prevents the air in the tube escaping. To overcome this surface tension effect, capillary tubes usually have to be filled by centrifugation to force the liquid into the tube, and such an arrangement is illustrated in for example in WO2005/019836.

For real-time PCR applications where fluorimetry is used to measure optically the formation of product, in addition to the difficulty of filling the tube per se, the presence of residual bubbles of air inside the capillary is problematic because these can move, and expand and contract, and possibly expel portions of the liquid sample, all of which can have optical effects which manifest themselves as noise in the data.

Preparing a capillary tube for PCR normally requires the user to pipette a sample (typically 10-30 microlitres in volume) into a cup formed at the top of the capillary, to place the capillary in a centrifuge, to spin the capillary at around 3,000 rpm for a few seconds (eg 20 seconds), to remove the capillary from the centrifuge, press in a cap and then place the capillary in a thermal cycler. This process can be automated in a single device, also as described in WO2005/019836.

In some circumstances, for example when space is at a premium or when the appropriate configuration of components is not possible, centrifugation may not be available as an option for transferring reaction mixes into capillaries. Another method of filling narrow aspect tubes in a way that avoids the formation of air bubbles is therefore required.

In particular, when using the system of the present invention however, it may be desirable to make the cartridge a different shape to more conveniently accommodate a sample vessel such as a tube. In a particular embodiment for example, the cartridge is generally rectangular in plan view, so that a tube may be accommodated lengthwise through the centre.

The cartridge may contain multiple parallel sample processing units stacked side by side. A non-centrifugal capillary-filling means was needed to fit in with the narrow aspect ratio of the individual modules.

The assay cartridge as described herein, generally uses a pipettor and in particular a pipettor as described in WO 2007/028966 for example to carry out steps such as the rehydration of freeze-dried PCR mix using a buffer containing purified nucleic acid from the sample.

The applicants have found that by modifying the pipettor to make the tip much longer and thinner (for example with an additional about 15-20 mm extension with an outside diameter of less than about 1 mm), it may be used to fill capillary sections of vessels. This is further facilitated by profiling the inside of the capillary section of the reaction chamber so that the upper part tapers smoothly inwards so as to guide the long capillary tip into place, the capillary section of the reaction chamber can be successfully filled without needing to carry out a centrifugation step.

The filling operation can successfully be executed by holding the reaction chamber in a fixed position for example on the cartridge. The pipettor is removeably held in an actuator which can be moved under fine control in a vertical direction. The actuator which holds the pipettor additionally has a co-axial plunger, also under fine control, that can be used to compress the diaphragm on the pipettor so as to draw in or expel liquid samples. The fine control is provided by stepper motors. The actuators can be programmed so that:

1) The pipettor fills with a set volume of PCR reaction mix approximately equal to the empty volume of the capillary
2) The pipettor is then positioned so that the open tip is positioned just above the bottom of the inside of the capillary tube
3) The pipettor is then slowly withdrawn and, as it rises up the capillary, the plunger is controllably depressed onto the diaphragm so as to expel the reagent mix into the capillary so that the capillary is filled without bubbles being formed.

Such methods for filling capilliary tubes have applications outside of the system described above, and thus this forms a further aspect of the invention.

Thus in a further aspect, the invention provides a method for filling a reaction vessel comprising a capillary tube which comprises introducing a filled pipettor with an elongated tip of a diameter less than that of the capillary tube into the tube, and depressing a plunger of the pipettor in a controlled manner so as to expel the contents into the capillary tube and concurrently, withdrawing the elongate tip of the pipettor from the capilliary tube at a speed commensurate with the delivery rate of liquid from the tube.

Modified pipettors, with elongate tips as well as modified reaction vessels with tapering sides above a capillary section of the vessel form yet further aspects of the invention.

The pipettor may take any suitable form, but in particular is a pipettor having an integrated cap member arranged to sealingly close the body, said cap member comprising a resilient diaphragm which is deformable in a downwards direction, as described for example in WO 2007/028966. Such pipettors are particularly suitable for use with mechanical actuators, such as may be found in robotic devices such as those of the preferred embodiments of the system of the present invention.

The invention will now be particularly described by way of example with reference to the accompanying diagrammatic drawings in which:

BRIEF DESCRIPTION OF DRAWINGS

FIG. 11 shows a plan view of the cartridge of FIG. 1 with a sample vessel entering the cartridge.

DETAILED DESCRIPTION OF THE PREFERRED EMBODIMENTS

Figure 1:
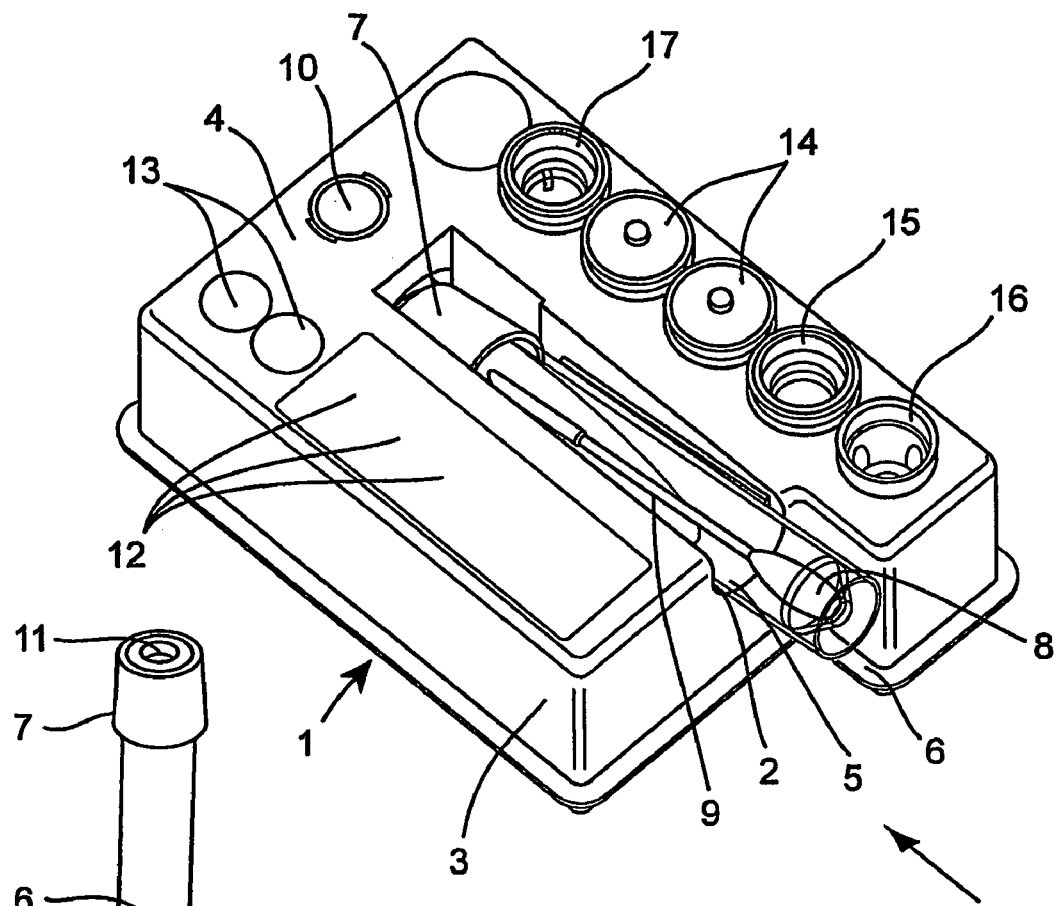
FIG. 1 shows a plan view of a cartridge useful in the system of the invention.

The cartridge shown in FIG. 1 includes a body section (1) which is of a rigid plastic material and is of generally oblong section. A clip feature is provided to facilitate location of the cartridge when it is placed in the instrument. A central longitudinal channel (2) is provided in the upper surface (3) of the body section (1). The channel (2) is open at one end but is does not extend the full length of the body section (1) so that it terminates in an end ridge (4) of the body section. The channel (2) has a generally curved base (5) and is shaped so that it could accommodate a tube (6) with a sealing cap (7). The channel 2 is inclined downwards towards the ridge (4) so that a liquid sample contained within the tube (6) will flow towards the cap (7).

In the illustrated embodiment, the tube accommodates a swab (8) which is fixed to the cap (7) by way of a support (9).

The cartridge also contains a reaction chamber (10). A piercing needle (not shown) or other piercing element extends between the chamber (10) towards the cap (7) with a piercing tip at the end adjacent the cap (7). The cap (7) suitably includes a piercable membrane (11) (FIG. 2) in the upper surface thereof.

When the tube (6) is in position in the channel (2), the cap (7) is sufficiently far removed from the piercing needle or element to ensure that it is not breached. However, the cartridge (1) is designed to be positioned within an apparatus (not shown), which is provided with an actuator able to apply pressure to the base of the tube (6) in the direction of the arrow. This forces the membrane (11) of the cap (7) against the piercing needle or element, which passes through the membrane (11) and thus breaches the seal.

Any liquid within the tube (6) is able to flow out through a channel in the needle or piercing element into the reaction chamber 10, where it may be subject to further processing. However, no operator contact with the contents of the tube (6) has taken place at this point and so the risk of contamination is minimised.

Figure 10:
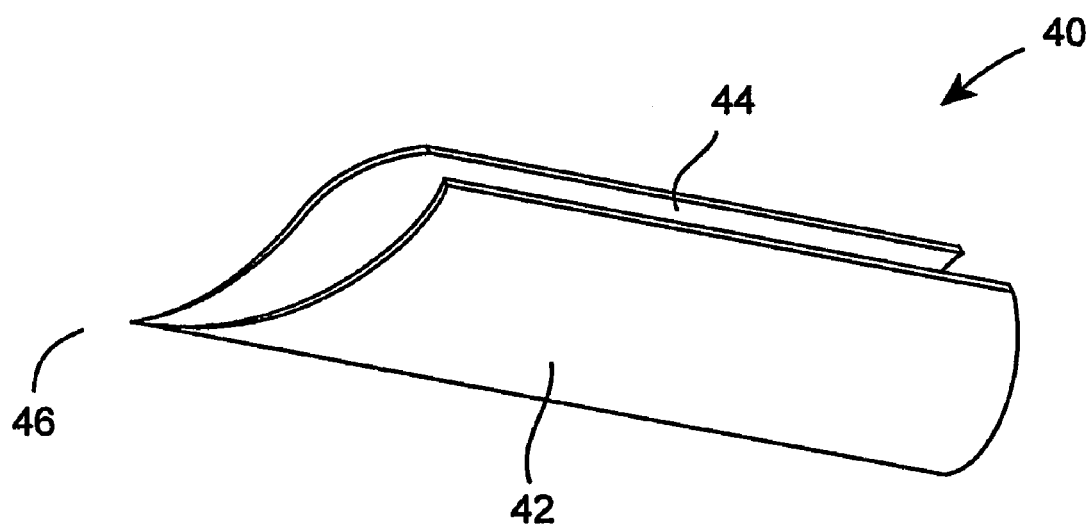
FIG. 10 illustrates a piercing element suitable for the cartridge shown in FIGS. 1-6.

FIG. 10 illustrates a piercing element suitable for use in the cartridge. The piercing element (40) is made from plastics material and has a cylindrical body (42) with one end cut obliquely to form a sharp point (46). A slit (44) runs along the top of the piercing element, which prevents an air lock being formed when the piercing element (40) pierces the cap of the tube, preventing the sample from flowing through the piercing element into the reaction chamber. This piercing element forms a neat hole of round cross section. However, piercing element s of other cross section could be used.

The cartridge (1) also includes in side sections a number of components or elements which may be utilised in an automated analytical process. For instance, it contains a number of foil sealed reservoirs (12) which may contain liquid reagents such as buffers, washes etc. which may be required for the desired processing of a sample. Others (13) may contain reagents such as solid reagents such as PCR beads useful in the subsequent processing of the sample.

In addition in this instance, the cartridge includes a series of movable components including two pipettors 14, a stopper 15 and a sheath 16 which may fit for example over a magnet used to move magnetic reagent beads from one chamber to another on the cartridge as required. These moveable components are accommodated within appropriately shaped apertures in the upper surface (3) of the body section (1). They are arranged so that an upper region projects above the upper surface (3) so that they are accessible for a grabbing arm of an apparatus. They may be provided with suitable annular flanges to facilitate this, or to assist in the lifting operation, for example as described in WO2005/019636.

In this case also, there is a provided in the cartridge (1), a reaction vessel (17) which is coated with an electrically conducting polymer, and so which, when connected to a suitable electrical supply, can subject the contents to a thermal cycling procedure such as that required for PCR.

The arrangement of this vessel will discussed in more detail hereinafter in relation to other illustrated embodiments.

Figure 2:
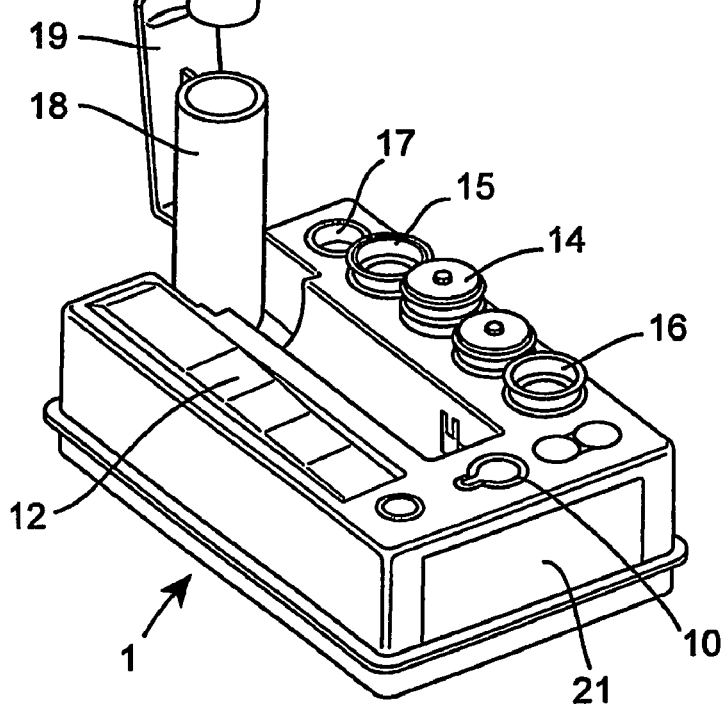
FIG. 2 is a schematic perspective view of a cartridge useful in the system of the invention which is about to receive a sample vessel.
Figure 3:
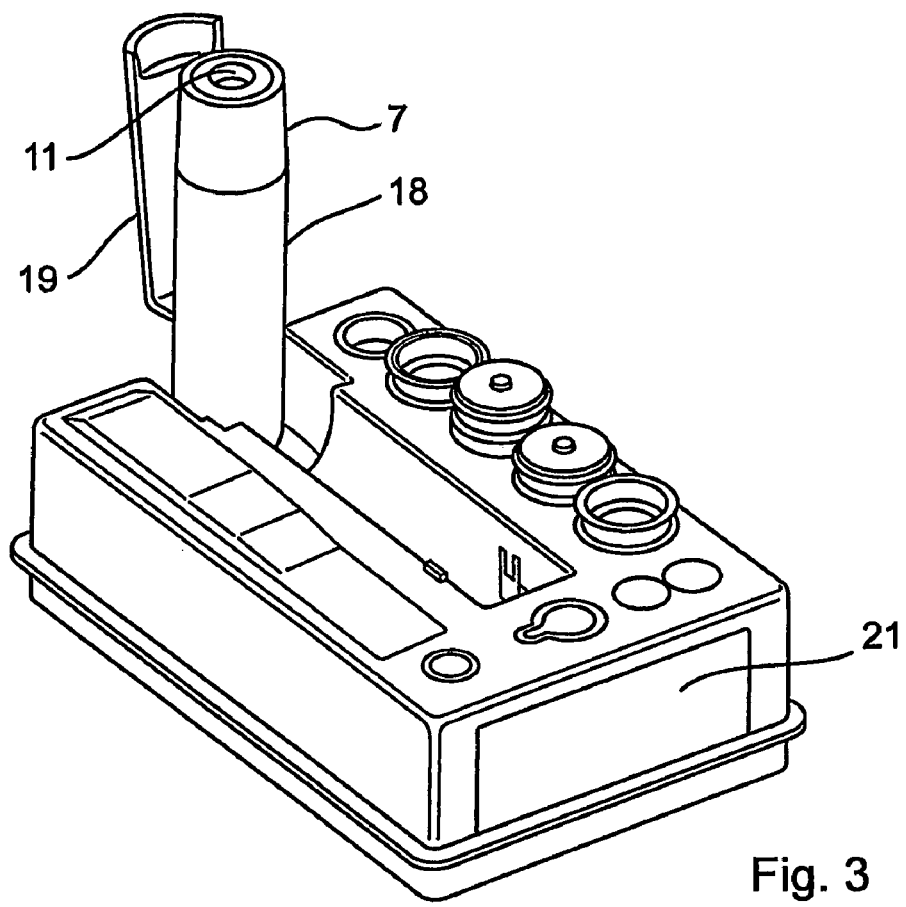
FIG. 3 is a perspective view of the cartridge of FIG. 2 with a sample vessel in place within the holder.

The cartridge illustrated in FIG. 2 contains many common elements although these are slightly differently arranged to suit the particular apparatus and chemical, biochemical or analytic procedure or assay being carried out. However, in this case, a holder (18) for the tube (6) is provided. The holder (18) is also tubular in shape and is capable of holding the tube (6) such that the cap (7) abuts against the end (FIG. 3).

The holder (18) may be retained against the cartridge body (1) in an upright sample vessel receiving position by means of a clasp (20) (FIGS. 5 and 6) disposed at the free end of the channel (2).

Figure 4:
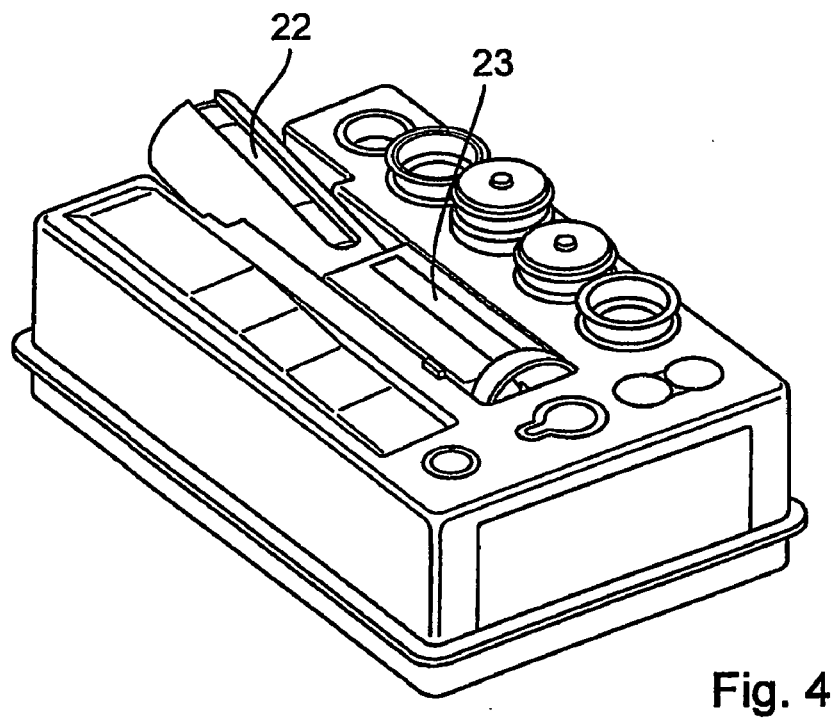
FIG. 4 is a perspective view of the cartridge of FIG. 3 in a "closed" position.

Once a tube (6) has been loaded into the holder (18), it is removed from the clasp (20), and inserted into the channel (2). A flange (19) provided on the side of the holder (18) is arranged to engage in a snap fit locking arrangement with a corresponding groove in the ridge (4) of the body section (1), but only if the tube (6) is snugly fitted into the holder (18) (FIG. 4).

At this point, the tube (6) and the cap (7) are substantially completely encased within the cartridge and holder and so are not accessible for fracture etc. A space (22) for a label for a bar-code reader to identify the cartridge and a window (23) to allow a bar-code on the sample tube to be read may be provided on the flange (19) and holder (18) respectively.

Sample labels may be applied at this point to the cartridge for example bar code labels which may be applied to an end region (21) of the body section (1), so as to facilitate tracking of the sample through the analytical procedure.

Figure 5:
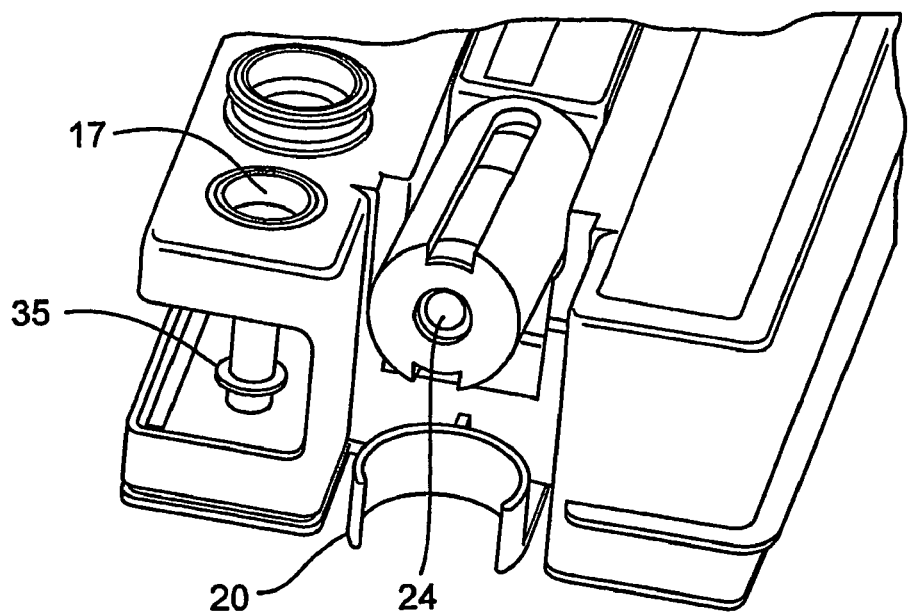
FIG. 5 is an end view of the cartridge of FIG. 4.
Figure 6:
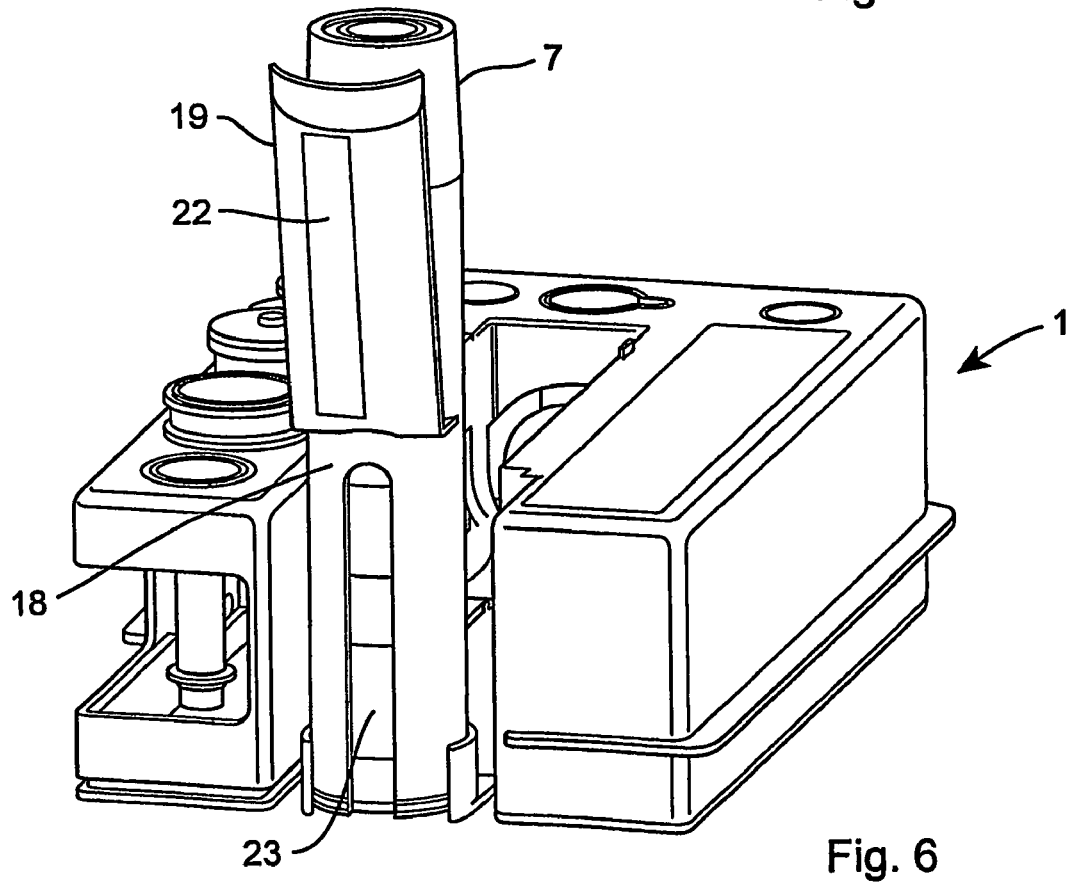
FIG. 6 is an end view of the cartridge of FIG. 3.

The base of the holder (18) includes a small aperture (24) (FIG. 5). The aperture (24) is shaped to allow an actuator of the apparatus into which the cartridge is introduced to pass through and so urge the tube (6) towards the piercing needle or piercing element provided at the region of the ridge (4)

Once the actuator has passed through the aperture (24), the cartridge is effectively "locked" and cannot then be opened. The actuator is then withdrawn whilst the sample tube remains in position at least until the end of the analytical procedure.

Figure 7:
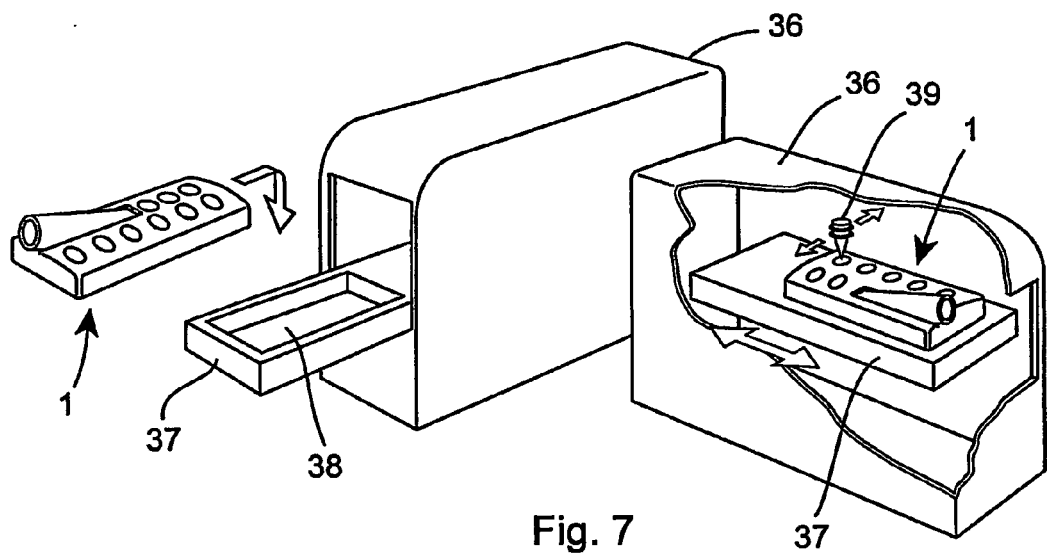
FIG. 7 is a schematic diagram showing how a cartridge of the invention may be introduced into a apparatus in which a chemical, biochemical or other type of assay or processing may be conducted.

The cartridge (1) is shaped so that it may be received into a receiving section of a suitable apparatus. This is illustrated schematically in FIG. 7. In that case, the cartridge receiving section of the apparatus (36) comprises a support (37) provided with a recess (38), into which the cartridge (1) snugly fits. The support (37) is retractable into the body of the apparatus (36), for processing. The support (36) is itself moveable (see arrows) so as to align any particular part of the cartridge (1) with an interacting element (39), which may be moveable in a vertical direction.

Figure 8:
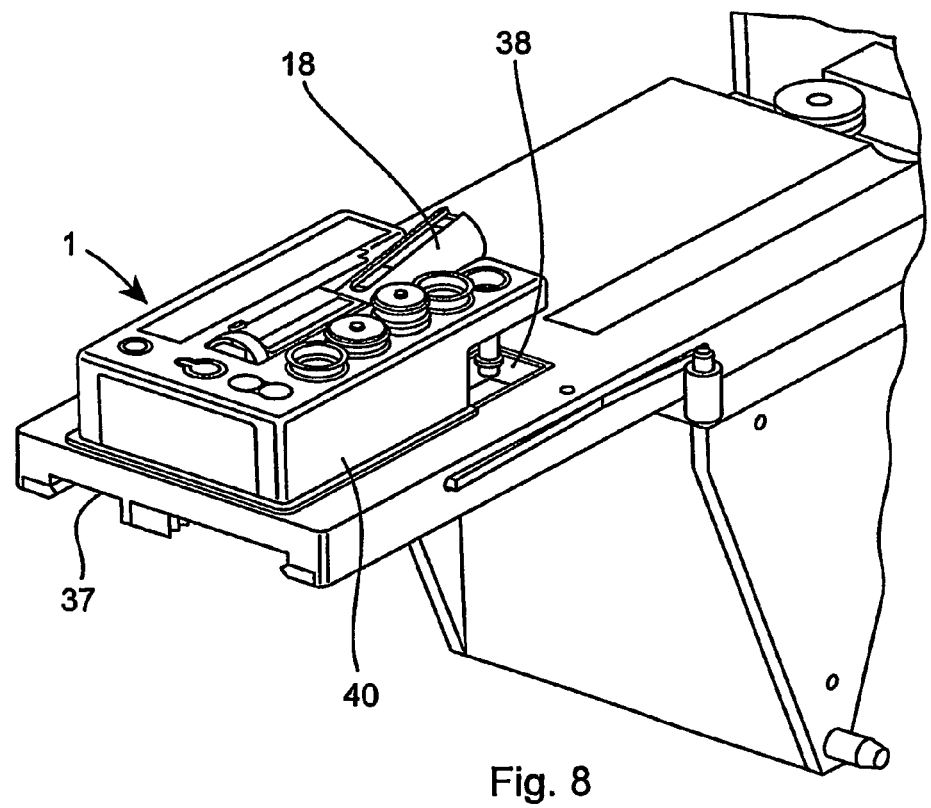
FIG. 8 illustrates a cartridge of the invention in position in a receiving section of an apparatus.

A similar arrangement, is illustrated in FIG. 8. In this case, the cartridge (1) is provided with a lip (40) which engages the upper surface of the support (37) when the cartridge is in position within the recess (38). The holder (18) is arranged so that when the support (37) is retracted into the body of the apparatus, the actuator for opening the tube (6) and can enter through the aperture (11) to release sample into the sample vessel (10) prior to the processing procedure. If required, locking or other engagement means may be provided to fix the cartridge (1) in position on the support (37).

Thus in use, a sample is collected for example for chemical, biochemical analysis, investigation or assay. If the sample is a liquid sample, it is suitably placed directly in a tube (6) which is sealed with a cap (7). Preferably the volume of the sample is known or is measured, in particular if the nature of the investigation being carried out is qualitative in nature. The sample tube may be inscribed with maximum and minimum fill lines to facilitate the dispensing of the liquid sample and to provide a means of checking that the sample volume is within the required limits. If the sample has been collected on a swab, then the swab (8) itself is placed in the tube together with a suitable and preferably known volume of eluent and the tube (6) is then sealed with a cap (7). The tube is then suitably shaken to ensure that any sample is transferred from the swab (8) to the eluent, although this may not be necessary if the volume of the liquid is sufficient to ensure that the swab remains immersed in the liquid.

Then either directly, or when it reaches a laboratory, the tube (6) is placed in a holder (18) of a cartridge. The holder is then inserted into the channel (2) of the body section (1) of a cartridge and the cartridge itself is labelled, before being placed into an appropriate cartridge receiving section of an apparatus (designed to effect the necessary procedures so as to effect the chemical, biochemical or analytical procedures or assays on the sample).

At this point, an actuator on the apparatus is caused to pass through the aperture (24) in the base of the holder (18) so as to urge the tube (7) towards the hollow piercing needle or other piercing element at the ridge end of the cartridge. Sufficient pressure is applied to the tube (6) by the actuator (24) to ensure that the rubber seal (11) in the cap (7) is breached by the needle or piercing element.

Because the tube (6) is inclined downwards towards the ridge (4), the liquid contained therein will run through the hollow piercing needle or piercing element directly into the reaction chamber (10) on the cartridge.

The apparatus is then able to effect processing, for example using robotic procedures known in the art. A vertically moveable arm is suitably used to effect the processing, whilst the cartridge is moveable, for example by Cartesian motion, so that the appropriate chamber or component on the cartridge is aligned with the arm at any one time.

The possibility for assay design using this procedure is limitless, as all that it is necessary to do in any particular case is to ensure that reagent containers on the cartridge and that suitable other components such as the moveable components described hereinbefore, are provided either on the cartridge or integrated appropriately into the apparatus.

A particular example of such a procedure is illustrated in WO2005/019836.

To summarise that procedure however, a sample within the chamber 10 which is known or suspected of containing cells of interest is subject to cell lysis. This may be achieved for example by preloading the chamber 10 with a chemical lysis agent such as guanidine hydrochloride, by adding such a reagent taken from a reagent container for example using a pipettor 14, by introduction of a sonicator which is suitably intergral with the apparatus or a combination of these. Where reagents are obtained from a sealed container 12 on the cartridge, they may be accessed following piercing of the foil lids with a cutter, which itself may be a moveable component on the cartridge or an integral part of the apparatus.

Magnetic beads which are suitably coated with a binding agent such an antibody specific for a particular target analyte or nucleic acid generically, such as "Magnesil®" silica beads are then introduced, for example using a magnet which is inserted into a sheath 16 and brought into contact with beads when it attraction is required (for example to pick the beads out of a container) and removed from the sheath when the beads are required to be deposited, for instance once the sheath has been positioned inside the reaction chamber 10.

After allowing the analyte such as any nucleic acid to become adhered to the beads, they may be removed from the reaction chamber (10) and placed into a different reaction chamber, which may have been foil sealed until the seal was broken by a suitable cutter before addition of the analyte. The beads may be moved through one or more wash chambers, optionally present on the cartridge, at this time if required.

Analyte may then be eluted from the beads for example by adding eluent, which is preferably hot, to a chamber containing the beads. Heating of the eluent may take place by introducing a heater provided on the apparatus, which is preferably encased within a protective disposable sheath 16 as described above. However, in the event that it is not, it may be subject to washing steps using wash liquids which may be contained in reagent chambers which are optionally on the cartridge.

Reagents suitable for carrying out a PCR reaction may also be prepared in a reaction chamber, for example by addition of a suitable buffer, in particular one containing purified nucleic acid extracted from the sample, to lyophilised beads of PCR reagents. Again, such procedures may be effected automatically within the apparatus by moving elements such as the cutter, pipettors etc so as to ensure that the appropriate reagent transfers occur.

Figure 9:
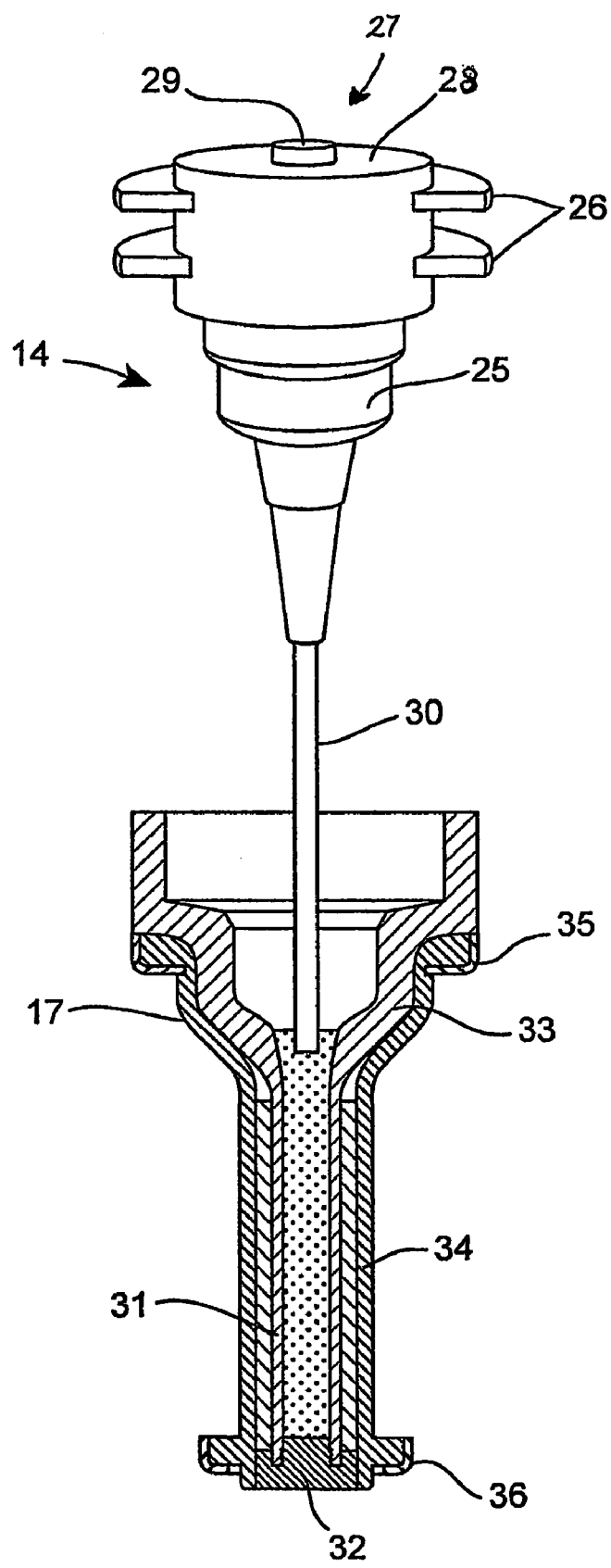
FIG. 9 is a schematic diagram illustrating a system for filling a capillary tube, which forms a further aspect of the invention.

Once a PCR reaction mixture has been prepared on the cartridge, it is suitably transferred into the reaction chamber 17, which is thermally cyclable as a result of an ECP (electrically conductive polymer) coating. Filling is achieved by means of a modified pipettor and the procedure is illustrated in FIG. 9.

As illustrated, the pipettor comprises a plastics body (25) provided with a series of annular flanges (26) which facilitate the collection of the pipettor by an arm of the apparatus. A cap member (27) has a resilient upper diaphragm (28) with a projection (29) intended to interact with an actuator provided on the apparatus, so as to allow controlled operation of the pipettor.

The lower section (30) of the pipettor is substantially elongate and of a sufficiently small diameter to enter a capillary tube (31). The capillary tube (31) is sealed at the lower end (32) and so forms a closed reaction vessel. The lower surface (32) is suitably transparent so that the progress of any reaction carried out in the vessel can be viewed. This means that, for example where the PCR is carried out in the presence of a fluorescent signalling system, it can be monitored throughout (real-time PCR). The upper portion (33) of the reaction vessel is of a wider cross section, but the walls in the region of the juncture of the upper portion (33) and capillary tube (31) are tapered so as to provide a guide for the lower section of the pipettor (30) as it enters the capillary tube (31).

An electrically conducting polymer layer (34) surrounds the capillary tube, and is connectable to an electrical supply by way of upper and lower electrical contacts (35, 36).

In use, the pipettor 14 is raised out of its housing with the cartridge by the interaction of the arm with the flanges 26, and lowered into a reaction chamber containing the prepared PCR reaction mixture. The pipettor actuator, driven by a stepper motor is deployed to depress the diaphragm (28) so as to draw the reaction mixture up into the pipettor body (25).

The pipettor is then raised out of the chamber by the moveable arm of the apparatus, the cartridge is moved so that the pipettor is located above the reaction vessel (17), and then lowered, until the lower section (30) of the pipettor (14) is substantially at the base (32) of the capillary tube.

The actuator for the diaphragm (28) is once again activated to expel the contents into the reaction vessel (17). At the same time, the arm is deployed to raise the pipettor (14) out of the reaction vessel (17). The movement of the arm and the actuator are co-ordinated so that the pipettor (14) leaves the capillary tube (31) at a suitable rate to provide bubble free filling.

The accuracy and controllability of the actuator and the arm as a result of the use of suitable controlling stepper motors, means that such an operation is possible.

Once the reaction vessel (17) has been filled in this way, a suitable cap or stopper may be applied to the upper section (33) to close the vessel. The electrical contacts 35, 36 may be connected so as to allow a thermal cycling process, for example a PCR reaction, to be conducted, within the reaction vessel (17) without further movement.

Suitably, the PCR includes one of the conventional signalling systems such as the Taqman™ or ResonSense™ methodologies and this is monitored through a transparent base (32) of the tube.

Once complete, the cartridge may be removed from the apparatus and discarded.

The systems and elements described herein therefore provide an effective and efficient way of conducting a variety of procedures, in particular chemical, biochemical or analytical assays, whilst minimising risks of contamination and false positive results which this may introduce.

The invention claimed is:

1. A sample delivery system comprising
   (i) a cartridge comprising a body section, wherein the body section is adapted to hold a holder for accommodating a sealed sample vessel so as to fix a position of a seal of the sample vessel in relation to the cartridge wherein at least a seal region of the sample vessel is substantially enclosed when held within the body section of the cartridge;
   (ii) a holder for accommodating the sealed sample vessel, which is insertable into the body section of the cartridge, the holder being moveable with respect to the body section from a sample vessel receiving position to a closed position in which the desired position of the sample vessel in relation to the cartridge is achieved;
   (iii) a locking mechanism for fixing the sample vessel in the closed position; and (iv) an apparatus adapted to receive said cartridge, said apparatus being provided with an opening system for opening said sealed sample vessel contained within the cartridge;

wherein in the closed position, the seal of the sample vessel is covered and is completely enclosed by the cartridge, holder or locking mechanism and is no longer accessible for removal or breach by an operator.

2. The system according to claim 1 wherein the locking mechanism comprises a snap fit tongue or flange, which is provided on the holder for the sample vessel and arranged to engage in a slot provided in the body section of the cartridge.

3. The system according to claim 1 wherein the locking mechanism is arranged so that it will not operate until the sample vessel is appropriately positioned within the holder.

4. The system according to claim 1 wherein the locking mechanism retains the sealed sample vessel in the body section.

5. The system according to claim 1 wherein the opening system comprises an actuator which is able to act on the sealed sample vessel within the holder within the cartridge in the apparatus and urge the seal of the sealed sample vessel into contact with a piercing needle or piercing element.

6. The system according to claim 1 which is adapted to hold a sealed tube as the sealed sample vessel.

7. The system according to claim 1 wherein the sealed sample vessel is provided with a cap having a piercable membrane in an upper surface thereof.

8. The system according to claim 1 wherein the sealed sample vessel is a sealable tube.

9. The system according to claim 8 wherein the sealable tube includes an integral swab.

10. The system according to claim 1 wherein the apparatus comprises further elements which allow the analysis or further investigation of a sample to be continued.

11. The system according to claim 1 wherein further elements which are useful in the subsequent procedures to which a sample is to be subjected are provided on the cartridge.

12. The system according to claim 11 wherein the further elements comprise reagent chambers for holding reagents or materials required to continue a chemical, biochemical, analytical or other assay of the sample.

13. The system according to claim 11 wherein the cartridge further comprises moveable components which are useful in or otherwise facilitate further chemical or biochemical reaction, analysis or assay of the sample.

14. The system according to claim 11 wherein the apparatus comprises a moveable arm, able to interact with any moveable component on the cartridge.

15. The system according to claim 1 wherein the apparatus comprises a processing component useful in further chemical or biochemical reaction, analysis or assay of a sample, which is reusable.

16. The system according to claim 15 which further comprises a sheath adapted to cover said component when in use.

17. The system according to claim 16 wherein the sheath is provided as a moveable component on the cartridge.

18. The system according to claim 16 wherein the sheath is of a thermally conducting plastic or elastomeric material.

* * * * *